United States Patent [19]

Resnick et al.

[11] Patent Number: 5,334,522
[45] Date of Patent: Aug. 2, 1994

[54] SYSTEM FOR ISOLATING AND PRODUCING NEW GENES, GENE PRODUCTS AND DNA SEQUENCES

[75] Inventors: Michael A. Resnick; Miroslav Radman, both of Chapel Hill, N.C.

[73] Assignee: United States/National Institutes of Health, Rockville, Md.

[21] Appl. No.: 860,233

[22] Filed: Mar. 27, 1992

Related U.S. Application Data

[63] Continuation of Ser. No. 457,557, Dec. 27, 1989, abandoned.

[51] Int. Cl.[5] .................. C12N 15/00; C12N 15/03
[52] U.S. Cl. ...................... 435/172.3; 435/252.3; 435/252.33; 435/240.1; 435/320.1
[58] Field of Search ............... 435/6, 91, 72.3, 320.1, 435/172.1, 240.1, 255, 240.2, 256, 252.3–252.35, 255.1, 255.2, 91.1, 1; 530/350; 536/22.1–24.5

[56] References Cited

U.S. PATENT DOCUMENTS

4,419,446 12/1983 Howley et al. .................. 435/69.1

OTHER PUBLICATIONS

Lewin; Science 237: 1570 (1987).
Reeck et al; Cell 50: 667 (1987).
Pharmacia P-L Biochemicals 1984 Product Reference Guide, 1984, pp. 5–10.
Wallace et al; Science 209: 1396 (1980).
Jaenisch, Science 240: 1468 (1988).
Schell, Science 237: 1176 (1987).
Gene Expression, vol. 2, Eucaryotic Chromosomes, 1974, Lewin, John Wiley & Sons, London, pp. 148–165.
Rayssiguier et al; Nature 343: 396 (1989).
American Type Culture Collection Catalogue, Fungi/Yeasts, 17th Ed., 1987, pp. 324–325.
Journal of Bacteriology, Oct. 1989, pp. 5339–5345, "Cloning and Nucleotide Sequence of DNA Mismatch Repair Gene PMS1 from *Saccharomyces cerevisiae*: Homology of PMS1 to Procaryotic MutL and HexB" W. Kramer M. S. Williamson, S. Fogel.
Molecular and Cellular Biology, Oct. 1989, pp. 4432–4439, "Heteroduplex DNA Correction in *Saccharomyces cerevisiae* Is Mismatch Specific and Requires Functional PMS Genes" B. Kramer, M. S. Williamson and S. Fogel.
Letters to Nature, vol. 328 Jul. 23, 1987, pp. 362–364, "The Role of heteroduplex correction in gene conversion in *Saccharomyces cerevisiae*" D. K. Bishop, M. S. Williamson, S. Fogel and R. D. Kolodner.
Pro. Natl. Acad. Sci. USA 87 (1990) vol. 87, pp. 7883–7887, Oct. 1990, "DNA mismatch repair in Xenopus egg extracts: Repair efficiency and DNA repair synthesis for all single base-pair mismatches" I. Varlet, M. Radman and P. Brooks.
Nature, vol. 295, Jan. 7, 1982, pp. 71–73, "Lower fidelity of RecA protein catalysed homologous paring with a superhelical substrate" C. DasGupta & C. M. Radding.
Cell. vol. 50, pp. 621–626, "Mismatch Repair and Recombination in *E. coli*" M. Jones, R. Wagner and M. Radman (1987).
Proc. Natl Acad. Sci. USA vol. 86, pp. 2276–2280, Apr. 1989 "Lack of DNA homology in a pair of divergent chromosomes greatly sensitized them to loss by DNA damage" M. A. Resnick, M. Skaanild and T. Nilsson-Tillgren.
Nucleic Acids Research, vol. 11 1983 pp. 5661–5669 "Formation of genes coding for hybrid proteins by recombination between related, cloned genes in *E. coli*" H. Weber and C. Weissmann.
Proc. Natl. Aca. Sci. USA vol 84, pp. 6496–6500, Sep. 1987 "Intramolecular recombination between partially homologous sequences in *Escherichia coli* and *Xenopus laevis* oocytes" J. P. Abastado, S. Darche, F. Godeau, B. Cami and P. Kourilsky.
Program and Abstracts Volume, Yeast Genetics and Molecular Biology 1989 Meeting "Engineering of Proteins by recombination of related cDNAs in *Saccharomyces cerevisiae*; shuffling of mammalian cytrochrome P-450 functions" D. Pompon and A. Nicholas.
Gene, 83 (1989) pp. 15–24 "Protein engineering by cDNA recombination in yeasts: shuffling of mammalian cytrochrome P-450 functions" D. Pompon and A. Nicolas.
Mol Gen Genet (1992) 12 pgs. "Recombinational repair of diverged DNAs: . . . " M. A. Resnick, Z. Zgaga, P. Heiter, J. Westmoreland, S. Fogel and T. Nilsson-Tillgren.
Fishel, Richard A. et al., "Gene Conversion in *Escherichia coli*". *J. Mol. Biol.*, 188: 147 (1986).
Bishop, Douglas K., "Repair of Heteroduplex Plasmid DNA after Transformation into *Saccharomyces cerevisiae*", *Molecular and Cellular Biology*, Oct. 1986, pp. 3401–3409, vol. 6, No. 10.

*Primary Examiner*—James Martinell
*Attorney, Agent, or Firm*—Knobbe, Martens, Olson & Bear

[57] ABSTRACT

A method of producing plasmids with heteroduplex DNA sequences, in which probe plasmids containing DNA inserts that correspond to probe sequences and test plasmids containing DNA inserts that correspond to a population of test sequences are first constructed. The vector portions of the plasmids used in these constructions have similar sequences. When test and probe plasmids are cleaved with appropriate restriction enzymes and then denatured to separate strands, complementary regions of the linear strands which correspond to vector sequences can anneal. The molecules that harbor test and probe inserts that are related by sequence complementarity form non-covalently closed circular molecules. These molecules can replicate after transformation into an appropriate host organism. There is a replication bias against plasmids which anneal through vector sequences, but which do not contain homologous probe and test inserts.

9 Claims, 1 Drawing Sheet

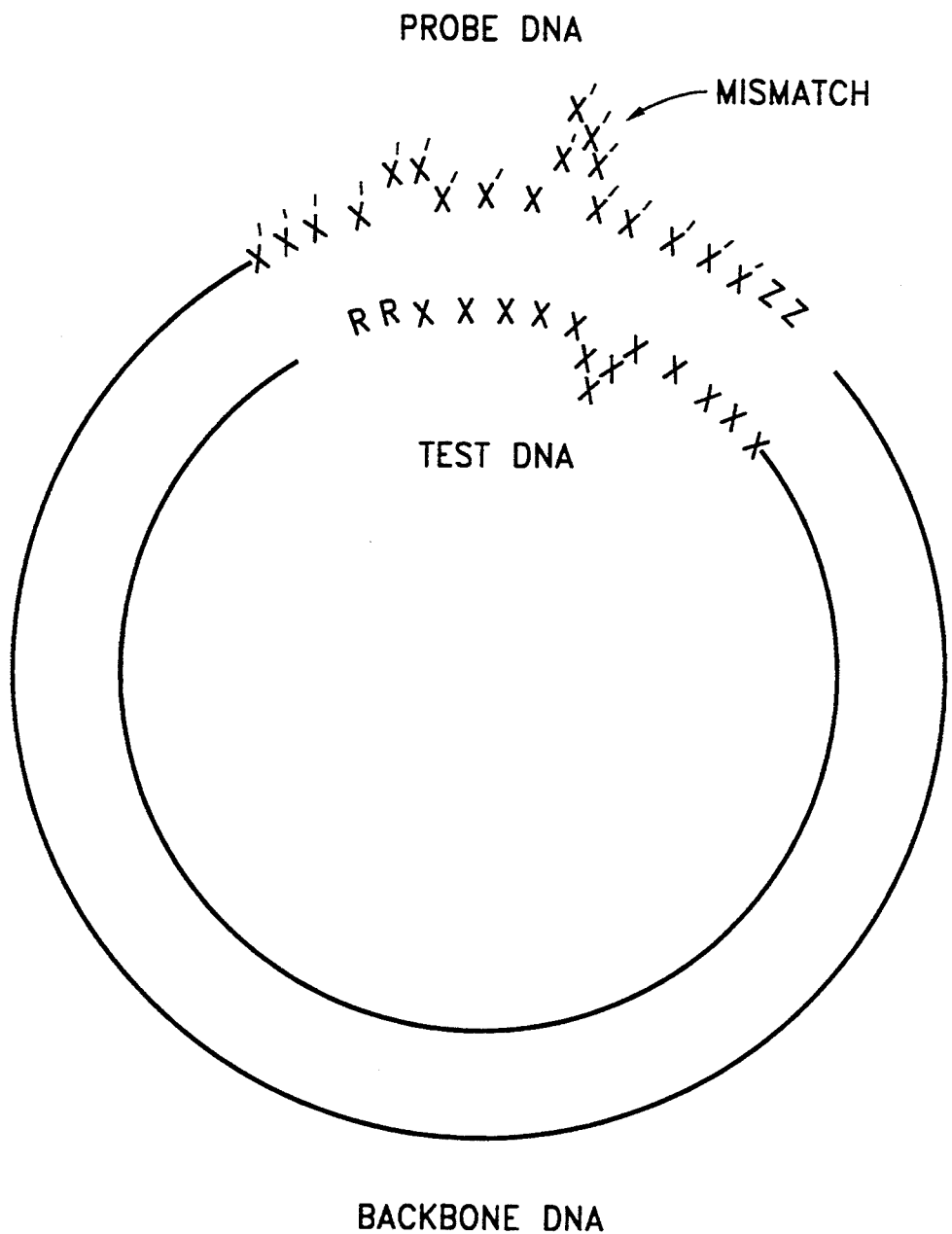

SYSTEM FOR ISOLATING AND PRODUCING NEW GENES, GENE PRODUCTS AND DNA SEQUENCES

This application is a continuation of application Ser. No. 457,557, filed Dec. 27, 1989, now abandoned.

The present invention is related generally to the identification, rapid isolation and manipulation of genes and DNA sequences with limited homology. More particularly, the present invention is directed to providing a divergent molecule selection system (DINOSS) using an in vitro intramolecular hybridization scheme enabling recovery, mapping, location, analysis and modification of members of a family of genes and DNA sequences related to a gene or a sequence of interest. The system provides a rapid method for in vitro isolation of DNA related to a known sequence and for the subsequent cloning or such related DNAs. It also provides a means for modification of the related DNA.

BACKGROUND OF THE INVENTION

It has been known that while genes of similar function exist within and between widely diverse organisms, the DNA sequences may differ considerably. Indeed, the homology in protein products may be much greater than the homology in DNA sequences due to the degeneracy of the genetic code. Furthermore, related sequences also exist that may or may not have a gene function. Since cloning of related genes within and between species is usually based on complementation of function, it has been difficult to identify, chromosomally locate and clone related genes and sequences between organisms due to the lack of DNA homology.

Recently, Rayssiguier et al, 1989, Nature, 342:842, demonstrated that in vivo recombination can be made to occur between divergent DNAs using appropriate mismatch repair mutants. However, Rayssiguier et al's methodology is limited and directed to an in vivo bimolecular system that occurs randomly between chromosomal molecules via recombination and is not designed for an in vitro scheme and does not provide a means for selection of related sequences from many different sources.

SUMMARY OF THE INVENTION

It is, therefore, an object of the present invention to provide an intramolecular in vitro scheme for interaction between homologous as well as divergent DNA sequences.

It is another object of the present invention to provide a rapid and simple in vitro molecular system for isolating DNA sequences related to a known DNA sequence or a DNA sequence of relatively low homology from unknown libraries of DNA and for the cloning of such sequences.

It is yet another object of the present invention to generate new and novel genes, gene products and DNA sequences.

Various other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 Illustrates the DIMOSS of the present invention. Novel recombinant circular molecules form as a result of intramolecular hybridization between complementary single-strands of related DNA sequences. The related DNAs are indicated by x x x x or x'x'x'x'. The probe DNA is the sequence for which related sequences are sought. The test DNA is a sequence that exhibits sufficient complementarity to the probe DNA to yield a stable hybrid, resulting in a circular molecule. The test DNA molecule and the probe DNA molecules are initially cloned in the same "backbone" vector DNAs. The only difference is that the probe DNA has a unique restriction site at one end and the test DNA has a unique site at the opposite end. When the two categories of molecules (probe and test) are denatured and renatured, the opportunity exists for annealing of test backbone DNA with probe DNA of opposite polarity. Subsequent less stringent hybridization conditions allow for hybridization of the related test and probe complementary DNAs, thus forming a circular molecule. Also diagrammed are regions where precise homology does not exist, resulting in mismatches.

DETAILED DESCRIPTION OF THE INVENTION

The above and various other objects and advantages of the present invention are achieved by a rapid and simple in vitro intramolecular system for interaction between homologous or divergent DNA sequences, comprising:

(a) a first cloning vector with a backbone and having cloned therein a probe DNA with a restriction site present at one end of said probe DNA, said restriction site being different from any other restriction site present anywhere in said vector or probe DNA, the probe DNA being a sequence for which related sequences are sought;

(b) a second cloning vector having the same backbone as the first cloning vector and having test DNA cloned therein with a restriction site present at an end of the test DNA opposite to the restriction site end of the probe DNA. the restriction site of the test DNA being different from any other restriction site present anywhere in said first or second vector probe or test DNA;

(c) an in vitro reaction medium and conditions suitable for restriction enzymes to cut the first and second cloning vectors at said restriction sites and for in vitro hybridization; wherein said first and second cloning vectors are mixed together in a proportion of about 10:1, respectively, then cut with suitable restriction enzymes in said reaction medium, the resulting DNA molecules then denatured and renatured, first under stringent conditions of about 70°–75° C. to allow annealing of vector backbone DNA, and then under slow cooling conditions to allow intramolecular annealing of related DNA sequences to form novel circular heteroduplex DNA sequences for subsequent propagation by transformation of suitable host cells or organisms that lack an effective mismatch repair system.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "intramolecular" as used herein means within one molecule after hybridization of complementary vector backbone portions of 5'→3' and 3'→5' single-strand molecules.

The term "bimolecular" as used herein applies to interactions between 5'→3' and 3'→5' single-strand molecules of limited or complete homology.

MATERIALS AND METHODS

A. Essential Components

1. A host organism such as *Escherichia coli*, yeast and the like. It is the recipient for the gene library and vectors described below. The types of strains to be used include various mismatch correction mutants, particularly mutU, mutS and mutY (Rayssiguier et al, supra).

2. Standard in vitro reaction conditions suitable for specific restriction enzymes and for DNA hybridization such as described in Berger et al, 1987, Guide to Molecular Cloning Techniques, Academic Press, N.Y.; and Sambrook et al, 1989, Molecular Cloning, Vol. I, II, III, Cold Spring Harbor, N.Y.

3. TEST DNA: Circular plasmids with cloned TEST DNA sequences .x.x.x.x.x.x. The TEST DNA sequences (i.e., sequences to be examined for DNA relatedness to PROBE DNA) could be contained in a library of cDNAs. Next to the TEST DNA Is a unique restriction site RR (to the left or the TEST DNA in this example).

```
..... ——————— RR.x.x.x.x.x.x ——————— .....
..... ——————— RR.x.x.x.x.x.x ——————— .....
```
[circular vector backbone]

4. PROBE DNA: Circular plasmid with PROBE DNA sequence x'x'x'x'x'. The plasmid "backbone" of the PROBE DNA and the TARGET DNAs (i.e., everything but x.x.x.x.x and x'x'x'x'x) are fully homologous. Next to the PROBE DNA sequence is a unique restriction site ZZ (to the right of the PROBE DNA in this example ).

```
..... ——————— x'x'x'x'x'ZZ ——————— .....
..... ——————— x'x'x'x'x'ZZ ——————— .....
```
[circular vector backbone]

B. PROCEDURE FOR USE OF COMPONENTS

1. Intramolecular Hybridization Method for Isolation of Related Sequences

The PROBE and TEST plasmids are cut at the RR and the ZZ sites thus generating linear plasmids. The PROBE DNA plasmid (x'x'x'x'x') is present in large excess. The plasmids are denatured and then renatured in two steps. The first renaturation is performed under stringent hybridization conditions (i.e., 70°-75° C.) to allow renaturatton of plasmid backbones. This will generate two major categories of linear molecules: one with single-stranded tails.

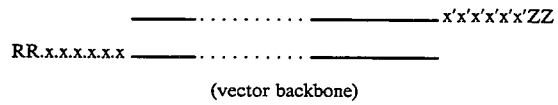

(vector backbone)

and second, the reconstituted linear PROBE DNA plasmid

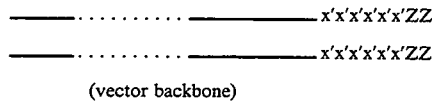

(vector backbone)

It is noted that due to renaturation of the excess PROBE DNA plasmids, this ks the predominant class of linear DNA molecules.

The second renaturation step simply involves slow cooling to room temperature (about 22°-24° C.) allowing intramolecular annealing of related sequences:

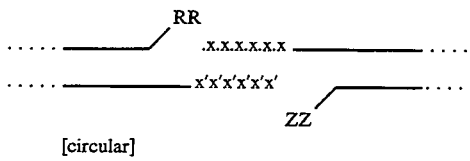

[circular]

Only those molecules containing protruding single strands with sequence related to probe DNA will be able to form circular molecules. Upon transfection of the appropriate *E. coli* mismatch repair deficient host, only the circular molecules will be propagated. The linear molecules will not be propagated or propagated at very low efficiency.. Thus, sequences related to the PROBE DNA are selectively isolated. Since some molecules may escape restriction cutting, It may be necessary to isolate the molecules with single-strand tails after the first (stringent) renaturation. This can be accomplished using a routine procedure involving the passage of the DNA through commercially available benzoylated-naphtoylated DEAE cellulose matrix. Both the double-strand linear (without tails) and the uncut circular molecules will flow through. The molecules with single-strand tails that are retained on the matrix can then be eluted.

To facilitate isolation of clones with only the related sequences, plasmids that are low copy in vivo can be used. Clonal segregants can be Isolated that have the specific TEST DNA sequence desired. To further aid in isolation or the clones with the desired sequence, a genetic marker such as lacZ (color marker) or transposon (drug-resistance) can be Included in one of the two strands of the TEST or the PROBE plasmid DNA. It Is noted that large looped structures In heteroduplex DNA are not subject to mismatch repair in *E. coil* (Dohet et al, 1987, *Mol. Gen. Genet.* 206: 181–184).

Modification of Related Sequences

Once related sequences are Isolated, a large population of DNA molecules specifically containing the above hybrids can be generated. By transforming such complex heteroduplex molecules into the appropriate hosts, different levels of "correction" to yield localized precise homology will result In modified genes and subsequently gene product. For example, *E. coli* mutants capable of localized repair of mismatches (Radman, 1989, *Genome* 31: 68–73) will generate sequences that differ from either x.x.x.x.x. or x'x'x'x'x'. Of course, this procedure can also be used to modify portions of genes. Since the procedure described herein can be used with any related sequence that will enable in vitro hybridization, the methodology extends to any DNA which has been isolated using this or a similar method.

EXAMPLE 1

Vectors and Cloning of Probe and Test DNA

Any or several standard *E. coli* based vectors are suitable, such as pBR322. The probe DNA is cloned into the vector as described in FIG. 1. At one end is a restriction site not present in the vector or the probe DNA. The cDNA or randomly cut DNA to be tested is cloned in a similar vector, preferably with a signal sequence as described below, so that an 8 base pair restriction cut site such as NOT1 or SFI (or even two adjacent sites) is at the opposite end. Having two rare cut sites assures that the vector can be cut without the cut being made in the cloned test DNA (it is highly unlikely that both will be found in any single piece of cloned DNA).

To assure identification of mixed colonies arising from hybrid molecules formed between test and probe DNAs (see below), the test DNA vector could contain an indicator sequence. This can be accomplished by including an inducible lacZ gene in the vector of either the test or the probe DNA. Transformants containing the gene will turn blue on X-gal containing medium when induced with IPTG. If the initial transformant contained a hybrid test/probe duplex, the colonies will be mixed in color due to segregation of test and probe molecules after several rounds of replication.

The cDNA or the randomly cut DNA is prepared using standard molecular biology methods such as described in Berger et al and Sambrook et al, supra. It is noted that the vector may include an inducible promoter next to the cloning site in order to more rapidly obtain information about the gene product of the isolated cDNA.

It is further noted that one-half of the test DNA plasmids will have the cloned test DNA in the wrong orientation. These will not lead to productive (hybrid circularized) molecules.

Preparation of Test DNA and Probe DNA Restriction-Cut Vectors

The vectors containing the probe DNA and the test DNA are cut separately with the appropriate restriction enzymes. It may be necessary for the test DNA to use two samples, each cut with one or the other 8 bp cutting restriction enzymes. The efficiency of cutting is determined using gel electrophoresis. Alternatively, because of the size variation, it may be necessary to run a parallel control to monitor cutting. If necessary, the DNA can be purified at this stage using standard filtering procedures or phenol extractions and the like.

C. Denaturation and Renaturation

Combine the cut probe DNA and the test DNA at a ratio of 10:1 in standard TRIS base pH 8,5 at a concentration of greater than or equal to 2-20 microgram/mi. Boil for 2 to 3 minutes.

For high stringency annealing of vector "backbone", bring to 0.2M NaCl, quick cool to 95° C., then slow cool to 75° C.

For the subsequent low stringency annealing, dilute 10 to 100 times in the same buffer (including 0.2M NaCl). The final volume will be approximately 2 to 4 ml containing up to 5 microgram DNA. Slow cool to room temperature (about 22°-24° C.). The slow cooling can be accomplished by placing samples in a heat block at 75° C. and shutting off the heat block (cooling time should be a few hours to overnight).

D. Transformation

The Hanahan procedure (Hanahan, D. in DNA cloning, Vol I, Glover, Ed. IRL Press, Washington, D.C. 1985. p 109). can be used to prepare cells for transformation. The cells to be used are mutS mutY [marY=-micA]so that all mismatch repair systems are inactivated (Nghtem et a], 1987, Proc, Natl. Acad. Scte. USA,85:2709; Radman, 1988, in Genetic Recombination, Kucherlapatt, Ed, Amer. Soc. Microbiol, Washington, D.C., p 169). Transformation is described in Berger et al and Sambrook et al. supra.

E. Analysis of Transformants

Four categories of transformants may arise.

1. Those that arose from rare molecules that were not initially cut by restriction enzymes.

2. Those that arose from linear molecules resulting from reannealing of probe DNAs. Although linear, they might, albeit very rarely, lead to transformants.

3. Those that arose from linear molecules resulting from reannealing of "backbones" of test and probe DNA. These are unlikely to contribute to the transformants.

4. Those that arose from circular molecules resulting from homologous Interactions between the single strands of probe and related test DNAs. Diagrammatic examples of interactions are shown In FIG. 1.

It is noted that clones of transformants 1, 2, and 3 mentioned above are expected to be very low in frequency.

F. Examination of Transformants

1. Minipreps of the transformant colonies that arise can be examined for DNA restriction patterns by standard methodology that would suggest the cloning of "related" (to probe) sequences.

2. If a mixed color vector assay system Is used, the colonies can be replicated to X-gal containing IPTG (tsopropylthtogalactoslde). The presence of mixed strands in the initial transforming DNA molecule will be indicated by blue and white colonies. Cells that give rise to blue colonies are purified and the plasmid DNA analyzed for its uniqueness as compared to the probe DNA vector.

3. The purified "related" DNA vectors can then be tested against probe DNA vector to establish relatedness.

G. Sequence Modification

Sequences of probe and homologous DNA can be modified using mutU *E. coli* mutants. The homologous DNA that is isolated on the basis of homology with the probe is purified and annealed with probe DNA. The hybrid DNA is transformed into mutU strains. These strains are helicase minus and thus hybrid molecules can be propagated. The strains have a functional "very short patch mismatch repair system" so that single (or a few base) mismatches can be corrected. Among the colonies that arise, many will have single base changes that match either the probe or the test DNA. As a result a library of altered sequences can be obtained that is derived from the information in either the test or the probe DNA.

Amounts of DNA Required

There are approximately $0.5 \times 10^{22}$ molecules/microgram of cloned DNA.

For an examination of mammalian cDNAs, assume approximately $10^{-4}$ to $10^{-6}$ frequency of representation of desired sequence.

To assure representation among cloned sequences, need 10 times the amount of DNA, therefore about $10^5$ to $10^7$ molecules.

Efficiency of transformation by circular molecules is approximately $10^{-2}$ to $10^{-6}$ per molecule. Thus, need about $10^7$ to $10^{10}$ molecules or about 0.2 microgram of test DNA and 2 microgram probe DNA.

For an examination of the total mammalian genome, assume $10^7$ kb and an average clone size of approximately 5 kb, therefore $2 \times 10^6$ pieces.

To assure representation, there should be greater than $2 \times 10^7$ molecules. Assuming an efficiency of transformation by circular molecules of approximately $10^{-2}$ to $10^{-6}$ per molecule, about $2 \times 10^9$ to $2 \times 10^{10}$ molecules are needed or about 0.4 micrograms test DNA and 4 mg probe DNA.

Of course, having obtained a novel recombinant cell or organism in accordance with the present invention, novel proteins produced by such new recombinants are easily identified and isolated by standard techniques of protein separation and purification well known to one of ordinary skill in the art.

It is understood that the examples and embodiments described herein are for illustrative purposes only and that various modifications or changes in light thereof will be suggested to persons skilled In the art and are to be included within the spirit and purview of this application and scope of the appended claims.

What is claimed is:

1. A method for producing plasmids with heteroduplex DNA sequences, comprising the steps of:
   (a) providing a first cloning vector with a first backbone molecule of DNA and having cloned therein a probe molecule of DNA wherein a first restriction site is present at an end of the probe DNA, said first restriction site being different from any other restriction site present anywhere in said first backbone or said probe DNA;
   (b) providing a second cloning vector having a second backbone molecule of DNA which is capable of annealing to said first backbone of said first cloning vector at between 75° C. and 95° C. in the presence of 0.2M NaCl, said second backbone having a test molecule of DNA cloned therein, the test DNA having a second restriction site, said second restriction site being present at an end of said test DNA, wherein the end of said test DNA having said second restriction site is distal to the end of said probe DNA having said first restriction site when said probe DNA and test DNA are annealed to each other, wherein said second restriction site is different from any other restriction site present anywhere in said first or second backbones, probe DNA or test DNA;
   (c) cutting said first cloning vector at said first restriction site with a restriction enzyme, thereby producing a first linear molecule;
   (d) cutting said second cloning vector at said second restriction site with a restriction enzyme, thereby producing a second linear molecule;
   (e) heat-denaturing said first and second linear molecules to obtain single-stranded DNA; and
   (f) hybridizing said linear molecules at between 75° C. and 95° C. in the presence of 0.2M NaCl to allow annealing of backbone DNA, followed by hybridization at between 22° C. and 75° C. in the presence of 0.2M NaCl to allow annealing of probe DNA and test DNA strands so that circular plasmids containing heteroduplex DNA sequences are obtained, wherein each strand of said circular plasmids contains a length of single-stranded DNA not annealed to the other strand of said plasmid, and wherein one end of each of said single-stranded lengths is not joined to the strand of said plasmid of which it is a part.

2. The method of claim 1, wherein said method is used to create a library of DNA molecules containing related DNA sequences, additionally comprising the steps of:
   (g) transforming a cell or single-celled host organism which has a functional mismatch repair system with said circular plasmids containing heteroduplex DNA sequences obtained in step (f);
   (h) repairing said one or more mismatches by means of the mismatch repair system of said cell or single-celled host organism, thereby producing a transformant containing a plasmid comprising the DNA sequences of the test DNA and probe DNA as modified by the mismatch repair system of said cell or organism; and
   (i) isolating said transformant.

3. The method of claim 2, wherein said cell is an *E. coli* cell.

4. The method of claim 2, wherein said cell is a yeast cell.

5. The method of claim 2, wherein said cell is a mammalian cell.

6. A method of producing a recombinant cell or organism, comprising the steps of:
   (a) transforming a cell which lacks a functional mismatch repair system with a double-stranded, circular plasmid produced in accordance with the method of claim 1, thereby producing a transformant containing a plasmid comprising the DNA sequences of the test DNA and probe DNA;
   (b) replicating said plasmid within said cell; and
   (c) isolating the transformant resulting from step (a).

7. The method of claim 1, wherein the amount of said first cloning vector containing said probe DNA which is provided, compared to the amount of said second cloning vector containing said test DNA that is provided, is approximately 10:1.

8. A double stranded circular plasmid containing heteroduplex DNA sequences wherein each strand of said plasmid contains a length of single-stranded DNA wherein said length of single-stranded DNA is not annealed to the other strand of said double-stranded plasmid, and wherein one end of single-stranded DNA is not joined to the strand of said plasmid of which it is a part wherein said plasmid is comprised of:
   (1) a first strand comprising (a) a backbone region, (b) a probe region, and (c) a first restriction site at the end of the probe region being different from any other restriction site present anywhere in said first strand of said plasmid and (2) a second strand comprising (a) a backbone region (b) a test DNA region, and (c) a second restriction site at the end of the test region and being different from any other restriction site present in said first or second strands and wherein the backbone regions of said first and second strands are capable of being annealed to one another at between 75° C. and 95° C. in the presence of 0.2M NaCl and wherein the restriction site at the end of the probe region on the first strand and the restriction site at the end of the test region on the second strand are distal to one another.

9. A cell that contains a double stranded circular plasmid containing heteroduplex DNA sequences wherein each strand of said plasmid contains a length of single-stranded DNA wherein said length of single-stranded DNA is not annealed to the other strand of said double-stranded plasmid, and wherein one end of single-stranded DNA is not joined to the strand of said plasmid of which it is a part wherein said plasmid is comprised of:

(1) a first strand comprising (a) a backbone region, (b) a probe region, and (c) a first restriction site at the end of the probe region being different from any other restriction site present anywhere in said first strand of said plasmid and (2) a second strand comprising (a) a backbone region, (b) a test DNA region, and (c) a second restriction site at the end of the test region and being different from any other restriction site present in said first or second strands and wherein the backbone regions of said first and second strands are capable of being annealed to one another at between 75° C. and 95° C. in the presence of 0.2M NaCl and wherein the restriction site at the end of the probe region on the first strand and the restriction site at the end of the test region on the second strand are distal to one another.

* * * * *